United States Patent [19]

Bishop et al.

[11] Patent Number: 5,041,599
[45] Date of Patent: Aug. 20, 1991

[54] CATALYTIC SYNTHESIS OF THIONOCARBAMATES FROM XANTHATES AND AMINES

[75] Inventors: Marshall D. Bishop; Lowell A. Gray, both of Bartlesville, Okla.

[73] Assignee: Phillips Petroleum Company, Bartlesville, Okla.

[21] Appl. No.: 560,622

[22] Filed: Jul. 30, 1990

[51] Int. Cl.$^5$ .............................................. C07C 67/02
[52] U.S. Cl. ................................................... 558/234
[58] Field of Search ....................................... 558/234

[56] References Cited

U.S. PATENT DOCUMENTS

| | | | |
|---|---|---|---|
| 2,913,327 | 11/1959 | Tilles et al. | |
| 3,772,345 | 11/1973 | Ham et al. | 558/234 |
| 3,907,854 | 9/1975 | Bolth et al. | 558/234 |
| 3,963,768 | 6/1976 | Millauer et al. | 558/234 |
| 3,975,264 | 8/1976 | Bolth et al. | 558/234 |
| 4,605,519 | 8/1986 | Bergman | 558/234 |
| 4,618,461 | 10/1986 | Bergman et al. | 558/234 |

OTHER PUBLICATIONS

Can. J. Chem. 38:2042-2052 (1960), McKay et al., The Preparation of Substituted Thionocarbamates.
J. Amer. Chem. Soc. 81:714-727 (1959), Harry Tilles, Thiolcarbamates Preparation and Molar Refractions.

*Primary Examiner*—Mary C. Lee
*Assistant Examiner*—Robert C. Whittenbaugh
*Attorney, Agent, or Firm*—Archie L. Robbins

[57] ABSTRACT

Catalytic processes for the synthesis of thionocarbamates by contacting xanthates, and amines, especially primary amines in the presence of at least one suitable catalyst. Suitable catalysts for these processes include finely divided metallic catalysts such as suspended nickel and precious metal(s); for example, Raney Nickel or platinum/palladium on carbon support. Reaction is carried out at a most preferred temperature of from about 70° C. to about 80° C. and for about 8 hours to about 12 hours for example.

12 Claims, No Drawings

CATALYTIC SYNTHESIS OF THIONOCARBAMATES FROM XANTHATES AND AMINES

BACKGROUND OF INVENTION

This invention relates to a process for the synthesis of thionocarbamates.

Thionocarbamates are well known compounds used as reagents in ore floatation. These compounds are also referred to as thiourethanes and are represented by the general formula:

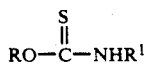

where R and $R^1$ are alkyl radicals.

The synthesis of thionocarbamates is also well known in the art. At the present time, there are two general methods for this synthetic process. The first method is a two-step reaction which involves reacting an alkali metal xanthate with an alkyl halide to form a diakyl xanthate. The xanthate is then reacted with an amine to form a thionocarbamate and a mercaptan. The second method is a one-step catalytic reaction which involves reacting a suitable xanthate and an amine in the presence of a suitable catalyst.

The problems and drawbacks of the first method are of common knowledge to those skilled in the art. Bolth, et al., (U.S. Pat. Nos. 3,975,264 and 3,907,854) background of the invention sections, which are hereby incorporated by reference, contain an excellent discussion of said problems and drawbacks. Furthermore, Bolth, et al., U.S. Pat. No. 3,907,854 represent a commercially accepted manufacturing process. In Bolth, et al., dissolved nickel salts (nickel sulfate) and palladium salts are used as catalysts. Palladium salts, for some inexplicable reasons seem to work better and are the catalyst of choice.

Although the Bolth, et al., process constitutes a significant improvement over the fomer two-step reaction process, it too, has its own drawbacks especially when nickel salts are used as catalyst. First, the nickel sulfate salt, because of its high solubility, completely goes into the aqueous phase. This makes its recovery and reuse economically unfeasible. Second, the process requires using relatively large quantities of nickel. Because nickel is costly, this further escalates the overall cost of the process. Third, the difficulty of recovering the nickel leads to potential environmental hazards: nickel, a toxic element, must now be disposed of while in the form of a salt dissolved in water.

These problems and the increased demand to synthesize thionocarbamates for the mining industry, provide a constant incentive for the development of alternative and better methods.

SUMMARY OF INVENTION

It is a general object of the present invention to provide a new and alternative process for the catalytic synthesis of thionocarbamates.

It is also an object of this invention to provide for a process for the catalytic synthesis of thionocarbamates using a metallic nickel catalyst.

It is a further object of this invention to provide for a process for the catalytic synthesis of thionocarbamates using a metallic precious metal or a combination of precious metals.

It is yet a further object of this invention to provide for a process for the catalytic synthesis of thionocarbamates which is economical, and environmentally safe.

In accordance with this invention, a process is provided for the synthesis of thionocarbamates from xanthates and amines using a finely divided metallic catalyst selected from nickel and precious metals.

DETAILED DESCRIPTION OF INVENTION

The ingredients useful in the practice of this invention include but are not limited to xanthates, amines and suitable catalysts.

Generally speaking, the actual practice of this invention comprises contacting a suitable xanthate and a suitable amine, in the presence of a finely divided metal catalyst selected from nickel and precious metals, under suitable reaction conditions to form a thionocarbamate. This process can also be represented by means of the chemical equation shown below:

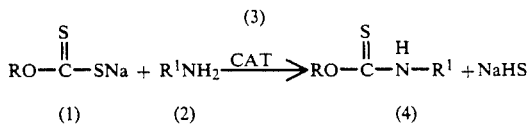

wherein (1) is a xanthate; (2) is an amine; (3) is a desired catalyst; and (4) is the desired thionocarbamate product.

The xanthates that are useful in the practice of this invention are those having from one to ten carbon atoms. These xanthates can be either commercially obtained or synthesized in the laboratory. Preferred, however, are the commercially available xanthates having from 2 to 5 carbon atoms. These xanthates are usually available as their sodium salts, and include but are not limited to ethyl, isopropyl, isobutyl, secbutyl and amyl xanthates. Amyl xanthate is also available as a potassium salt.

The most preferred of the xanthates is sodium isopropyl xanthate.

The amines useful in the practice of this invention are secondary and primary amines. Examples of secondary amines are dimethylamine, di-n-propyl amine, diethylamine, α-phenylethyl amine, and similar compounds. Examples of primary amines are methylamine, ethylamine, propyl amine, isopropyl amine, and like compounds. The primary amines are preferred.

Activated nickel catalysts and precious metal(s) catalyst are generally suitable in the practice of this invention. By the term activated nickel catalyst, is meant, metallic nickel which has been treated by heat, radiation, in the presence of a reducing agent, or by some other substance, so as to increase the catalytic activity of the nickel catalyst. These activated nickel catalysts will generally vary in particle size, settling characteristics, aluminium content, and the presence or absence of transition metals promoters. Raney Nickel is the preferred activated nickel catalyst useful in the practice of this invention. Generally, the activated nickel catalyst will not be on a support, but optionally it can be loaded on inactive supports such as bentonite and ceramic.

The term precious metals as used herein, includes palladium, rhodium, platinum, and ruthenium. Generally, the precious metal will be on a support. These precious metals can be used individually or in combination. A preferred example of a precious metals catalyst is palladium/platinum on a refractory material such as carbon or silica.

The reaction conditions for this invention are as follows: the temperature is generally in the range of from about 50° C. to about 120° C., with a preferred range of from 50° C. to 90° C., and a most preferred range of from 70° C. to 80° C. The time needed to complete the reaction generally ranges from about 2 hours to about 20 hours, with a preferred time of from 4 hours to 16 hours, and most preferred reaction time of from 8 hours to 12 hours. It is noted that the yield obtained seems to be generally directly proportional to the reaction time. However, after 20 hours, no measurable increase in yield is observed.

The general ratio of the reactants is a 1:1 molar ratio of xanthate and amine. Preferred, however, is such a ratio that contains about a 10% excess amine. The quantity of catalyst needed when nickel is used generally is in the range of from about 0.05 grams to 10 grams per mole of xanthate. However, 0.3 gram to 5 grams nickel per mole of xanthate is preferred. When a precious metal is used, the metal generally is in an amount within the range of 0.005 to 1, preferably 0.01 to 0.1 gram per mole of xanthate.

Whether using an activated nickel catalyst or a precious metals combination catalyst, the process of the invention is essentially the same. This process comprises of the following steps: Weighing out a suitable quantity of the xanthate powder and dissolving it in water to form a solution in a suitable reaction vessel. This dissolution process is unnecessary if the xanthate is obtained as a solution. Adding suitable quantities of a suitable amine, and a suitable catalyst to the reaction vessel. Monitoring the reaction to conform to the reaction conditions recited in the previous paragraphs. This monitoring and/or controlling of reaction conditions is important for at least two reasons. First, excessively high temperatures promote the unbeneficial decomposition of the xanthate reactant. Second, controlling reaction conditions minimizes the evaporation of the amine reactant. Thus, product yield depends on the suitability of reaction conditions.

Upon completion of the reaction, an organic phase and an aqueous phase are formed. The aqueous phase contains sodium hydrogen sulfide, unreacted amine, xanthate, and any impurities present in the original xanthate. When stirring or other agitation is complete the nickel, or other precious metals employed being in the insoluble metallic form settles to the bottom and can be removed by filtering off the liquid phase or the liquid phase can just be decanted off. The thus easily recovered nickel or other precious metals employed can be returned to the reaction as catalyst and if needed can be purified and/or reactivated for subsequent reuse. The organic phase contains primarily the desired thionocarbamate. Phase separation is effectuated using any convienent devices and/or methods known in the art. The thionocarbamate product can then be washed and analyzed for purity using conventional methods. The reaction can be carried out on a batch or continuous scale.

EXAMPLES

EXAMPLE I

To a 2-L glass reactor containing 1200 ml of deionized water, 604 g of 81% active commerical sodium isopropyl xanthate (3.09 moles) was added while stirring. After the xanthate was completely dissolved, 16.3 g (0.062 moles) of nickel sulfate ($NiSO_4.6H_2O$) was added to the reactor. Subsequent to the addition of nickel sulfate, 307 ml of 70% active monoethyl amine (3.77 moles) solution was added.

The reactor was then heated to 80° C. and maintained at this temperature (80° C.) for 16 hours followed by cooling to room temperature. The reaction product, thionocarbamate, was separated using a separatory funnel and 314 g (2.13 moles) of N-ethyl, O-isopropyl thionocarbamate was recovered. This represents a yield of 69% based on the amount of xanthate reactant used.

EXAMPLE II

This example illustrates the inventive process employing Raney Nickel.

The experiment was carried out using the same procedure as in Example I with the exception that, instead of a nickel salt, 13.5 g of Raney Nickel catalyst suspended in water was added to the reactor as catalyst and after the reaction was complete, the reaction product was filtered to remove the still insoluble metallic nickel. 287 g N-ethyl, O-isopropyl thionocarbamate (287 g) was then recovered. This represents a yield of 63% based on the amount of xanthate reactant used.

This example demonstrates that Raney Nickel is an effective catalyst for the reaction between xanthates and amines in the synthesis of thionocarbamate, and is easily removed after the completion of the synthetic process.

The Raney Nickel used was Type B113W from Degussa Corporation, and had 93.49% nickel, 6.2% aluminum, a pH in the aqueous suspension of $\leq 10.5$, a bulk density of 1.3 Kg/L, a particle size of less than $200\mu$, with a particle size distribution of less than $32\mu$ 40%, and less than $50\mu$ 60%.

EXAMPLE III

This example illustrates that even a minimal amount of Raney Nickel is effective to catalyze the reaction between xanthates and amines.

The experiment was carried out using the same procedure as in Example II except that 400 ml instead of 1200 ml of deionized water, 0.5 g instead of 13.5 g of Raney Nickel and one-half quantity of all other reactants was used. A total of 135 g of the desired thionocarbamate was recovered, representing a 59.4% based on the amount of xanthate reactant used.

The result of this example shows that minimal amounts of Raney Nickel catalyst are effective in catalyzing the reactions between xanthates and amines.

EXAMPLE IV

This example illustrates the synthesis of thionocarbamate from xanthate and amine catalyzed by mixed palladium and platinum on activated carbon.

To a stirring 1L reactor containing 400 ml of deionized water, 336.5 g of 72% active commercial sodium isopropyl xanthate (1.53 moles) was added. After the xanthate was completely dissolved, 0.75 g of commercial mixed Pt-Pd catalyst on an activated carbon support (51.2% moisture, 2% Pt and 8% Pd on dry basis), (type EF1053) obtained from Degussa Corporation was added to the reactor followed by adding 158 ml of 70% monoethylamine to the reaction mixture.

The reactor was heated to and maintained at 80° for 16 hours followed by cooling to room temperature. The reaction mixture was then filtered to remove the still insoluble metallic Pt-Pd. The reaction product, N-ethyl, O-isopropyl thionocarbamate (78 g) was recovered using a separatory funnel. This represents a yield of 34.7% based on the amount of xanthate reactant used.

The result indicate that, Pt-Pd on activated carbon is an effective catalyst useful in the process of producing thionocarbonate from the reaction between xanthates and amines.

While this invention has been described in detail for the purpose of illustration, it is not to be construed as limited thereby but is intended to cover all changes and modifications within the spirit and scope thereof.

What is claimed is:

1. A process for the synthesis of thionocarbamates comprising contacting a xanthate and an amine in the presence of a metallic catalyst wherein said metal of said catalyst is insoluble and is selected from the group consisting of Raney Nickel or a combination of platinum and palladium.

2. A process according to claim 1 wherein the amine is a primary amine selected from the group consisting of methylamine, ethylamine, propylamine, and isopropylamine.

3. A process according to claim 1 wherein contacting said xanthate, amine, and catalyst occurs under reaction conditions comprising a reaction temperature within a range from about 50° C. to about 120° C.

4. A process according to claim 3 wherein said reaction conditions include a reaction time from about 8 hours to about 12 hours.

5. A process according to claim 1 wherein said metal of said catalyst is Raney Nickel.

6. A process according to claim 5 wherein said catalyst is on a support selected from the group consisting of bentonite and ceramic.

7. A process according to claim 1 wherein said metal of said catalyst is a combination of platinum and palladium.

8. A process according to claim 7 wherein said catalyst is on a support selected from the group consisting of carbon and silica.

9. A process according to claim 8 wherein the catalyst comprises a 1:4 weight ratio of platinum and palladium respectively on a carbon support.

10. A process for the synthesis of thionocarbamates comprising contacting a xanthate and an amine in the presence of 0.01 to 0.1 grams of a 1:4 weight ratio of platinum-palladium catalyst, the catalyst being on a carbon support, said contacting occurring at a temperature of about 70° C. to 80° C. for about 8 hours to 12 hours, to produce a reaction mixture, thereafter seperating the platinum-palladium catalyst from the reaction mixture, and thereafter recovering N-ethyl, O-isopropyl thionocarbamate.

11. A process for the synthesis of thionocarbamates by contacting sodium isopropyl xanthate and monoethylamine in the presence of 0.3 to 5 grams of suspended Raney Nickel catalyst having a particle size of less than 200 microns, per mole of the xanthate, said contacting occurring at a temperature range from about 70° to 80° C. for about 8 hours to 12 hours, to produce a reaction mixture, thereafter separating the Raney Nickel from the reaction mixture by filtration, and thereafter recovering N-ethyl, o-isopropyl thionocarbamate.

12. A process according to claim 3 wherein said reaction temperature is within a range from 70° C. to 80° C.

* * * * *